United States Patent [19]

Amoss et al.

[11] 4,261,887
[45] Apr. 14, 1981

[54] PEPTIDE COMPOSITIONS

[75] Inventors: Max S. Amoss, College Station, Tex.; Michael W. Monahan, San Francisco; Wylie W. Vale, Jr., La Jolla, both of Calif.

[73] Assignee: The Salk Institute for Biological Studies, San Diego, Calif.

[21] Appl. No.: 849,014

[22] Filed: Nov. 7, 1977

Related U.S. Application Data

[60] Division of Ser. No. 509,835, Sep. 27, 1974, Pat. No. 4,072,668, which is a continuation-in-part of Ser. No. 413,314, Nov. 6, 1973, abandoned.

[51] Int. Cl.$^3$ ............................................ C07C 103/52
[52] U.S. Cl. .......................................... 260/112.5 LH
[58] Field of Search ............................. 260/112.5 LH

[56] References Cited

U.S. PATENT DOCUMENTS

| 3,880,825 | 4/1975 | Sakakibara et al. | 260/112.5 LH |
| 3,896,104 | 7/1975 | McKinely et al. | 260/112.5 LH |
| 3,937,695 | 2/1976 | Sarantakis | 260/112.5 LH |
| 4,072,668 | 2/1978 | Amoss et al. | 260/112.5 LH |

OTHER PUBLICATIONS

Yanaihara, et al., Biochem. and Biophys. Res. Communication, 51, 1973, pp. 165–173.
M. Monahan et al., Biochemistry 12, 1973, pp. 4616–4620.
W. Vale et al., Science, 176, 1972, pp. 933 & 934.

Primary Examiner—Delbert R. Phillips
Attorney, Agent, or Firm—Fitch, Even, Tabin, Flannery & Welsh

[57] ABSTRACT

Peptides have been synthesized which influence the secretion of gonadotropins by the pituitary gland of mammalians, including humans. Some of the peptides promote the release of gonadotropins, while other peptides inhibit the release.

9 Claims, No Drawings

PEPTIDE COMPOSITIONS

The invention described herein was made in the course of work under a grant or award from the Department of Health and Human Services.

This is Divisional of United States Patent Application Ser. No. 509,835, now U.S. Pat. No. 4,072,668, filed Sept. 27, 1974, which is a continuation-in-part of Ser. No. 413,314, filed Nov. 6, 1973, and now abandoned.

The present invention relates generally to novel peptide compositions having influence on the release of luteinizing hormone by the pituitary gland in mammalians, including humans. More particularly, the present invention is directed to novel peptide compositions which enhance or inhibit the release of luteinizing hormone by the pituitary gland.

The pituitary gland is attached by a stalk to the region in the base of the brain known as the hypothalamus. The pituitary gland has two lobes, the anterior and posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or molecules that travel through the blood stream to various organs and which, in turn, stimulate the secretion into the blood stream of other hormones from the peripheral organs. In particular, follicle stimulating hormone and luteinizing hormone are release by the pituitary gland. These hormones, in combination, regulate the functioning of the gonads to produce testosterone in the testes and progesterone and estrogen in the ovaries, as well as regulating the production and maturation of gametes. These hormones are sometimes referred to as gonadotropins or gonadotropic hormones.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly luteinizing hormone. For convenience, luteinizing hormone is hereinafter referred to as LH. The hypothalamic hormone which acts as a releasing factor for LH is referred to herein as LRF wherein RF stands for "releasing factor" and the L signifies that the hormone releases LH. As discussed below, LRF has been isolated and identified.

It has been demonstrated that female mammalians who have no ovulatory cycle and who show no pituitary or ovarian defect begin to secrete normal amounts of the gonadotropins, LH and FSH (follicle stimulating hormone) after the administration of LRF. The administration of LRF is suitable for the treatment of those cases of infertility where the functional defect resides in the hypothalamus. Ovulation can be induced in female mammalians by the administration of LRF. However, the dosage level of LRF required to influence ovulation may sometimes be high. Accordingly, it would be desirable to provide peptide materials with an enhance potency to effect the secretion of gonadotropins. It would also be desirable to provide peptide materials which inhibit secretion of gonadotropins. Such inhibiting peptides can be used as contraceptives.

The principal object of the present invention is to provide peptide materials which influence the release of gonadotropins by the pituitary gland of mammalians, including humans. Another object of the present invention is to provide peptide materials which have an enhanced effect on secretion of gonadotropins by the pituitary gland of mammalians, including humans. A further object of the present invention is to provide peptide materials which have an enhanced inhibitory effect on the secretion of gonadotropins by the pituitary gland of mammalians, including humans. Another object of the present invention is to provide peptide materials which have an enhanced effect on secretion of gonadotropins by the pituitary gland of mammalians, including humans.

These and other objects of the present invention will become more apparent from the following detailed description.

Generally, in accordance with the present invention, peptides have been synthesized which influence the secretion of gonadotropins by the pituitary gland of mammalians, including humans. Some of the peptides enhance the release of gonadotropins, while other peptides inhibit the release when compared with known peptides which enhance or inhibit release of gonadotropins.

A peptide has been isolated from ovine hypothalamus fragments which has been identified as being the releasing factor for the secretion of the gonadotropins. This peptide has been characterized as a decapeptide having the following structure:

pGlu-His-Trp-Ser-Tyr-Gly-Leu-Arg-Pro-Gly-NH$_2$

For convenience, this decapeptide will be sometimes referred to hereinafter as LRF decapeptide or LRF.

Peptides are, of course, compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino groups is identified by numbering the amino groups from left to right. In the case of LRF, the hydroxyl portion of the carboxyl group has been replaced with an amino group (NH$_2$). The abbreviations for the individual amino acid groups above are conventional and are based on the trivial name of the amino acid: where pGlu is pyroglutamic acid, His is histidine, Trp is tryptophan, Ser is serine, Tyr is tyrosine, Gly is glycine, Leu is Leucine, Arg is arginine and Pro is proline. Except for glycine, amino acids are of the L-configuration unless noted otherwise.

It has now been discovered that the substitution of D-Ala or D-Lys for Gly in the 6-position of the LRF decapeptide provides a peptide material having from 3 to 10 times greater potency than does LRF to effect the release of luteinizing hormone and other gonadotropins by the pituitary gland of mammalians. The releasing effect is obtained when the substituted peptide is introduced into the blood stream of a mammalian.

It is known that substitution of various amino acids for His (or the deletion of His) at the 2-position of the LRF decapeptide produces peptide materials having an inhibitory effect on the release of luteinizing hormone and other gonadotropins by the pituitary gland of mammalians. In particular, varying degrees of inhibition of the release of luteinizing hormone are obtained when His is deleted (des His) or replaced by Asp, Cys, D-Ala, or Gly. It has been further discovered that the inhibitory effect of those peptides modified at the 2-position can be greatly enhanced when D-Ala or D-Lys is substituted for Gly in the 6-position of the decapeptides. For example, the peptide: pGlu-Trp-Ser-Tyr-D-Ala-Leu-Arg-Pro-Gly-NH$_2$ is 3 times more potent as an inhibitor for the release of gonadotropins than is the same peptide where Gly is present in the 6-position rather than D-Ala.

The effect of the substitution of D-Ala or D-Lys in the 6-position of the LRF decapeptide is completely surprising. The substitution of L-Ala for Gly in the 6-position of LRF provides a peptide which has only 3 percent of the potency of LRF decapeptide for effecting the release of luteinizing hormone by the pituitary gland. The substitution of other amino acids for Gly at the 6-position provides peptide materials with varying levels of potency in respect to the release of luteinizing hormone and other gonadotropins but are not comparable to the use of D-Ala. For example, the substitution of D-Val for Gly provides a peptide having 30 percent potency, substitution of D-Leu for Gly provides a peptide material having 60 percent potency, the substitution of D-Pro provides a peptide material having 10 percent potency. As used herein, percent potency refers to the potency compared to the LRF decapeptide.

The peptide compositions of the present invention are represented by the following formula:

pGlu-R$_1$-Trp-Ser-Tyr-R$_2$-Leu-Arg-Pro-Gly-NH$_2$ wherein R$_1$ is deleted or is selected from His, Gly, Asp, Cys, des His, and D-Ala and R$_2$ is selected from D-Lys and D-Ala. When both D- and L- forms of an amino acid are possible, the L- form is intended unless otherwise specifically indicated.

In general, when R$_1$, is Gly, or deleted (des His) the peptide compositions are antagonistic to the secretion of gonadotropins stimulated by LRF. When R$_1$ is His, the peptide compositions effect release of gonadotropins and are more effective than LRF for this purpose.

Various substituted LRF peptides, as described above, have been found to have further enhanced properties when ProNHCH$_2$CH$_3$ is substituted for Pro-Gly-NH$_2$ at the 9-position. For example, a potent peptide with greater effectiveness than LRF is provided when R$_1$ is His, R$_2$ is D-Ala and Pro-NHCH$_2$CH$_3$ is substituted for Pro-Gly-NH$_2$. A peptide antagonistic to secretion of gonadotropins is provided when R$_1$ is Gly, R$_2$ is D-Ala and Pro-NHCH$_2$CH$_3$ is substituted for Pro-Gly-NH$_2$.

Peptides in accordance with the present invention were prepared by solid phase synthesis on a benzhydrylamine resin. The benzhydrylamine resin was prepared in accordance with the following:

(Step A.) FRIEDEL-CRAFTS reaction:

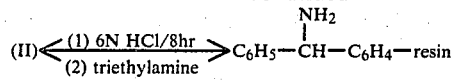

(Step. B.) LEUKART'S reductive amination:

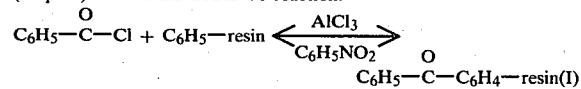

(Step C.) Hydrolysis, neutralization:

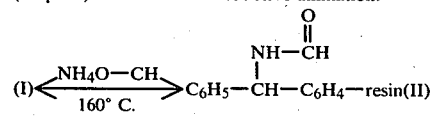

The resin used was a copolymer of styrene and 1 percent by weight of divinylbenzene.

t-Butyloxycarbonyl (BOC) protective group was used for all N$^a$ amino groups. Benzyl ethers were used for the side chain protection of Ser and Tyr. All amino acids, other than D-Ala and Gly were of the L-configuration.

Coupling of a residue was carried out for 5 hours in dimethylformamide (DMF) using a 10-fold excess of BOC reagent and dicyclohexylcarbodiimide (DCC) activating reagent. The first residue is attached to the benzhydrylamine resin by an amide bond. The coupling reaction was monitored by a ninhydrin test, as reported by Kaiser et al. Anal. Biochemi. 34 (1970) 595.

The deblocking procedure consisted of a 20 minute treatment in TFA containing 5 percent, 1,2-ethanedithiol, followed by neutralization with triethylamine (Et$_3$N) in DMF. Numerous washes with MeOH and CH$_2$Cl$_2$ followed each step.

The cleavage of the peptide from the resin and complete deprotection of the peptide takes place very readily at 0° C. with hydrofluoric acid (HF). Anisol was added to the resin prior to treatment with HF. After the removal of HF, under vacuum, the resin was treated with ethylacetate, filtered and the peptide was then eluted with acetic acid and water. The combined acetic acid-water extracts were evaporated and subjected to purification.

Purification of the peptide was effected by partition chromatography in a gel filtration column using the elution system; n-Butanol; Acetic acid; Water (4: 1:5; volume ratio). This was followed by simple gel filtration using 0.5 N acetic acid as eluent.

Using the above method, the peptide compositions set forth below in Tables I and II were prepared. The peptide compositions were assayed in vitro and in vivo. The in vitro assay was made using a five day old primary culture of dispersed rat pituitary cells. The LH secreted in response to the peptide compositions was assayed by specific radioimmunoassay for rat LH. The peptide compositions were applied to the culture at a level of $3 \times 10^{-5}$ M. The potency of these peptide compositions which stimulate secretion of gonadotropins is expressed in terms of percent LRF potency wherein LRF has a potency of 100. For those peptide compositions which are antagonistic to secretion of gonadotropins, the culture was inoculated with $3 \times 10^{-5}$ M of LRF and the molar ratio of the peptide required to suppress secretion of LH generated by the LRF was determined.

The effectiveness of the peptide compositions which stimulate secretion of gonadotropins was determined in vivo by intravenous injection of 100 nanograms of the peptide into rats. The rats were chronically ovariectomized and were treated with estrogen and progesterone prior to assay. The LH level was determined in plasma by solid phase radioimmunoassay for rat LH. For those peptide compositions which are antagonistic to secretion of gonadotropins, the rats were injected with 100 nanograms of LRF and the molar ratio of the peptide required to suppress section of LH generated by the LRF was determined.

The results of the in vivo and in vitro tests are set forth below in Table I for those peptide compositions having greater effectiveness than LRF. The results for those peptide compositions antagonistic to secretion of gonadotropins stimulated by LH are set forth below in Table II.

TABLE I

| Peptide Composition | Percent LRF Potency | |
|---|---|---|
| | In Vitro | In Vivo |
| pGlu-His-Trp-Ser-Tyr-Gly-Leu-Arg-Pro-Gly-NH$_2$(LRF) | 100% | 100% |
| pGlu-His-Trp-Ser-Tyr-D-Ala-Gly-Leu-Arg-Pro-Gly-NH$_2$(LRF) | 400% | 500% |
| pGlu-His-Trp-Ser-Tyr-D-Lys-Leu-Arg-Pro-Gly-NH$_2$(LRF) | 500% | 1,000% |
| pGlu-His-Trp-Ser-Tyr-D-Glu-Leu-Arg-Pro-Gly-NH$_2$(LRF) | 80% | 30% |
| pGlu-His-Trp-Ser-Tyr-D-Ala-Leu-Arg-Pro-NHCH$_2$CH$_3$ | 1,500% | 300% |

TABLE II

| Peptide Composition | Molar ratio necessary to produce inhibition | |
|---|---|---|
| | In Vitro | In Vivo |
| pGlu-deleted-Trp-Ser-Tyr-Gly-Leu-Arg-Pro-Gly-NH$_2$ | 2,000 | 3,000 |
| pGlu-deleted-Trp-Ser-Tyr-D-Ala-Leu-Arg-Pro-Gly-NH$_2$ | 700 | 500 |
| pGlu-Gly-Trp-Ser-Tyr-D-Lys-Leu-Arg-Pro-Gly-NH$_2$ | 700 | 500 |
| pGlu-Gly-Trp-Ser-Tyr-D-Ala-Leu-Arg-Pro-NHCH$_2$CH$_3$ | 700 | 500 |

It has been determined that only picogram quantities are necessary at the pituitary gland to provide the release or the suppression of release of gonadotropins by the peptide compositions of the invention. Generally, administration of 500 nanograms of LRF per kilogram of body weight of a mammal provides a significant release of gonadotropins by the pituitary gland. Those peptide compositions of the invention which stimulate release of gonadotropins will produce the same response as LRF but lower levels proportioned to their potency.

Those peptides having enhanced potency in respect to the release of luteinizing hormone and other gonadotropins by the pituitary gland are valuable for the treatment of mammalians reproductive disorders. The administration of the peptide material into the blood stream of the mammalian results in the secretion of appropriate amounts of the gonadotropins. Thus, these peptide materials can be used for the treatment of those cases of infertility where a functional defect exists in the relationship between the hypothalamus and the pituitary system. Ovulation and/or spawning can be induced in vertebrates by the administration of the peptide materials. Substitution of D-Ala or D-Lys for Gly in the 6-position has marked advantages, in that potency is increased, the amount required is reduced, and oral administration is practical.

Those peptides which have an inhibitory effect on the release of luteinizing hormone can be used to suppress the secretion of normal amounts of the gonadotropins and can be used as contraceptives. In addition, they can be used to inhibit the inappropriate secretion of gonadotropins in situations such as precocious puberty.

What is claimed is:

1. A peptide which inhibits the release of gonadotropins by the pituitary gland having the formula pGlu-R$_1$-Trp-Ser-Tyr-D-Lys-Leu-Arg-Pro-X wherein R$_1$ is selected from Gly, Asp, Cys, D-Ala and des R$_1$ and wherein X is selected from Gly-NH$_2$ and NHCH$_2$CH$_3$.

2. A peptide in accordance with claim 1 wherein R$_1$ is Gly.

3. A peptide in accordance with claim 1 wherein R$_1$ is Asp.

4. A peptide in accordance with claim 1 wherein R$_1$ is D-Ala.

5. A peptide in accordance with claim 1 wherein R$_1$ is des R$_1$.

6. A peptide in accordance with claim 1 wherein X is Gly-NH$_2$.

7. A peptide in accordance with claim 1 wherein X is NHCH$_2$CH$_3$.

8. A peptide in accordance with either claim 4 or 5 wherein X is NHCH$_2$CH$_3$.

9. A peptide which inhibits the release of gonadotropins by the pituitary gland having the formula pGlu-Trp-Ser-Tyr-D-Lys-Leu-Arg-Pro-Gly-NH$_2$.

* * * * *

UNITED STATES PATENT AND TRADEMARK OFFICE
CERTIFICATE OF CORRECTION

PATENT NO. : 4,261,887
DATED : April 14, 1981
INVENTOR(S) : Max S. Amoss et al.

It is certified that error appears in the above—identified patent and that said Letters Patent is hereby corrected as shown below:

Column 3, lines 59 and 60, the vertically aligned two pairs of O and C atoms should be interconnected by a double bond.

Column 3, lines 58 and 66, the double-headed arrows should be single-headed arrows pointing to the right.

Column 4, line 4, the double-headed arrow should be a single-headed arrow pointing to the right.

Column 5, correct Table I to read as follows:

TABLE I

| Peptide Composition | Percent LRF Potency | |
|---|---|---|
| | In Vitro | In Vivo |
| pGlu-His-Trp-Ser-Tyr-Gly-Leu-Arg-Pro-Gly-$NH_2$ (LRF) | 100% | 100% |
| pGlu-His-Trp-Ser-Tyr-D-Ala-Leu-Arg-Pro-Gly-$NH_2$ | 400% | 500% |
| pGlu-His-Trp-Ser-Tyr-D-Lys-Leu-Arg-Pro-Gly-$NH_2$ | 500% | 1,000% |
| pGlu-His-Trp-Ser-Tyr-D-Glu-Leu-Arg-Pro-Gly-$NH_2$ | 80% | 30% |
| pGlu-His-Trp-Ser-Tyr-D-Ala-Leu-Arg-Pro-$NHCH_2CH_3$ | 1,500% | 300% |

Signed and Sealed this

Twenty-ninth Day of September 1981

[SEAL]

Attest:

Attesting Officer

GERALD J. MOSSINGHOFF
Commissioner of Patents and Trademarks